(12) United States Patent
Hoeffler et al.

(10) Patent No.: US 6,815,202 B2
(45) Date of Patent: Nov. 9, 2004

(54) IN VITRO SYNTHESIS OF A LAYERED CELL SORTED TISSUE

(75) Inventors: Warren K. Hoeffler, San Carlos, CA (US); Deborah Finlay, San Francisco, CA (US)

(73) Assignee: Xgene Corporation, San Carlos, CA (US)

( * ) Notice: Subject to any disclaimer, the term of this patent is extended or adjusted under 35 U.S.C. 154(b) by 64 days.

(21) Appl. No.: 10/013,124

(22) Filed: Dec. 7, 2001

(65) Prior Publication Data

US 2002/0120950 A1 Aug. 29, 2002

Related U.S. Application Data

(60) Provisional application No. 60/254,781, filed on Dec. 8, 2000.

(51) Int. Cl.[7] .................................................. C12N 5/00
(52) U.S. Cl. ........................ 435/347; 435/325; 435/410
(58) Field of Search ................................. 435/347, 325, 435/401

(56) References Cited

FOREIGN PATENT DOCUMENTS

| WO | WO 97/18296 A1 | 5/1997 |
|----|----------------|--------|
| WO | WO 99/45770 A1 | 9/1999 |

OTHER PUBLICATIONS

U.S. patent application Ser. No. 09/037,191, Hoeffler et al., filed Mar. 9, 1998.

Boyce, S.T. et al. (Apr. 1993). "Skin Anatomy and Antigen Expression After Burn Wound Closure with Composite Grafts on Cultured Skin Cells and Biopolymers," *Plastic Reconstructive Surgery* 91(4):632–641.

Cooper, M. and Hansbrough, J.F. (Feb. 1991). "Use of a Composite Skin Graft Composed of Cultured Human Keratinocytes and Fibroblasts and a Collagen–GAG Matrix to Cover Full–Thickness Wounds on Athymic Mice," *Surgery* 109(2):198–207.

Faust, J.B. and Meeker, T.C. (May 1992). "Amplification and Expression of the bcl–1 Gene in Human Solid Tumor Cells Lines," *Cancer Res.* 52:2460–2463.

Funk, W.D. et al. (May 2000). "Telomerase Expression Restores Dermal Integrity To In Vitro–Aged Fibroblasts In A Reconstituted Skin Model," *Experimental Cell Research* 258:270–278.

Fusenig, N.E. et al. (1994). "Epithelial–Mesenchymal Interactions Regulate Keratinocyte Growth and Differentiation In Vitro" Chapter 4 In *The Keratinocyte Handbook*. Irene M. Leigh et al., Cambridge University Press, pp. 71–94.

Hansbrough, J.F. et al. (Oct. 1989). "Burn Wound Closure With Cultured Autologous Keratinocytes and Fibroblasts Attached to a Collagen–Glycosaminoglycan Subtrate," *JAMA* 262(15):2125–2130.

Leigh, I.M. et al. (1994). *The Keratinocyte Handbook*, Cambridge University Press, Great Britain (Table of Contents) pp. ix–xi.

Meyers, C. (May 1996). "Organotypic (Raft) Epithelial Tissue Culture System for the Differentiation–Dependent Replication of Papillomavirus," *Symposium: Infectious Disease* pp. 201–210.

Trainer, D.L. et al. (1988). "Biological Characterization and Oncogene Expression in Human Colorectal Carcinoma Cell Lines," *Int. J. Cancer* 41:287–296.

Yannas, I.V. et al. (Jan. 1982). "Wound Tissue Can Utilize a Polymeric Template to Synthesize a Functional Extension of Skin," *Science* 215:174–176.

Wang, C.K. et al. (Apr. 2000). "Spontaneous Cell Sorting of Fibroblasts and Keratinocytes Creates an Organotypic Human Skin Equivalent," *The J. of Invest. Dermatol.* 114(4):674–680.

Patent Abstract of Japan, (Sep. 12, 1984) vol. 008, No. 199 (C–242) corresponding to Japanese Patent Publication No. 59–088423 published on May 22, 1984 entitled "Production of human tomorous cell degeneration factor (TDF)" and Derwent Dialog® English abstract, 2 pages total.

Lee, Kwang Hoon (Dec. 2000) "Tissue–engineered human living skin substitutes: development and clinical application" *Yonsei Medical Journal* 41(6):774–779.

Schoop, V. M. et al., (Mar. 1999) "Epidermal organization and differentiation of hacat keratinocytes in organotypic coculture with human dermal fibroblasts" *Journal of Investigative Dermatology*, New York, NY, US, 112(3):343–353.

*Primary Examiner*—Leon Lankford
(74) *Attorney, Agent, or Firm*—Morrison & Foerster LLP

(57) ABSTRACT

The present invention relates to a layered cell sorted tissue that is formed in vitro. The tissue is generated by the spontaneous sorting of cells from a homogenous cell mixture into discrete layers by cell type. Connective tissue components, such as fibronectin, may be used to manipulate orientation of the layers during the cell sorting process. The layered cell sorted tissue may be used as a skin graft for burns, wounds, and ulcers. The tissue may also be used in assays to determine effects of chemicals or drugs on human tissue in vitro as well as provide an in vitro assay for tumor cell metastasis.

20 Claims, 4 Drawing Sheets

IN VITRO SYNTHESIS OF A LAYERED CELL SORTED TISSUE

RELATED APPLICATIONS

This application claims the benefit under 35 U.S.C. § 119(e) of U.S. Provisional Application No. 60/254,781, filed Dec. 8, 2000, which is hereby incorporated by reference.

FIELD OF THE INVENTION

The present invention is directed to a layered tissue cultivated in vitro, i.e., in tissue culture. In particular, the invention relates to a layered tissue that is generated by sorting of cells from a homogenous cell mixture into discrete layers by cell type that are connected by a basement membrane. Methods for forming and using the in vitro cell sorted layered tissue are also described.

BACKGROUND OF THE INVENTION

Advances in tissue culture technique have led to the development of artificial tissue and promising research for the development of artificial organs. However, artificial tissues are generally still inferior to their counterpart in vivo. For example, homeostatic regulation and many specific cell interactions that regulate cell proliferation and organization are lost so that in many structural aspects, the artificial and native tissues are not equivalent. The addition of various hormones and growth factors to culture media has helped to more closely simulate in vivo conditions, but remains an insufficient remedy.

The co-culturing of keratinocytes and fibroblasts, for example, has been documented as being "antagonistic", resulting in an overgrowth of fibroblasts in Leigh et al. (1994). *The Keratinocyte Handbook,* Cambridge University Press, Great Britain. In one approach, researchers have attempted to restrict fibroblast growth in culture by using irradiated fibroblasts in feeder layers, but substantial improvement in epithelial structure and correct expression of differentiation markers was not found. Currently, cultured epithelia is being created using organotypic culture techniques (Hansbrough et al., *JAMA* 262:2125–2130 (1989); Cooper et al., *Surgery,* 109:198–207 (1991); and Boyce et al., *Plast. Reconstr. Surg.,* 91:632–641 (1993)) or methods that employ forming epidermal and dermal layers separately, and then sandwiching them together, or by relying on a synthetic support to generate the keratinocyte and/or fibroblast layer (Yannas et al., *Science,* 215:174 (1982)). In all these techniques, the epithelial tissues are formed using a preformed support.

Furthermore, products that employ artificial tissue are currently being marketed. For example, Dermagraft® (Advanced Tissue Sciences, La Jolla, Calif.) is a polylactic, polyglycol, or polygalactoside material upon which fibroblasts are cultivated. Autologous keratinocytes are then seeded onto these materials.

GraftSkin® (Organogenesis, Inc., Boston, Mass.) is a product where fibroblasts are cultivated on a collagen based substrate.

AlloDerm® (Life Cell Corp., The Woodlands, Tex.) constitutes human or pig's skin in which the basal membrane and dermal matrix remain intact. The tissue is stored at approximately −80° C. until ready to be used, then seeded with autologous fibroblasts and keratinocytes prior to application onto a patient.

However, these, and most other products in development do not allow the in vitro reconstruction of a functional epidermal-dermal junction or basement membrane. Thus, dissection or "blistering" between the keratinocyte and fibroblast layers tends to occur.

Another method described in U.S. patent application Ser. No. 09/037,191, which is herein incorporated by reference in its entirety, relates to the in vivo creation of an artificial layered tissue formed by sorting of keratinocytes and fibroblasts from a homogenous mixture of cells into discrete epidermal, dermal, and basal keratinocyte layers. However, the tissue generated in this manner could not be used in applications requiring sterility, i.e., where contamination by cells or factors from an intermediate host presents a problem for the final host receiving the graft.

Therefore, new artificial tissues that can be created in a sterile environment are needed. Furthermore, an artificial tissue that preserves native tissue architecture is needed, in particular, the formation of a proper epidermal-dermal junction, including a basement membrane is needed.

SUMMARY OF THE INVENTION

The present invention is a layered cell sorted tissue that includes a discrete first cell layer and a discrete second cell layer that are formed in vitro by the spontaneous sorting of cells from a homogenous cell mixture. The first cell layer may include any cell type, but preferably includes epithelial cells. In a preferred embodiment, the first cell layer includes keratinocytes. The keratinocytes are preferably obtained from an early passage number such as passage 2 or 3. Other cell types that may used in the first cell layer are CaCo2 cells, A431 cells, and HUC18 cells. The second cell layer may also include cells of any type, but preferably includes mesencyhmal cells. In a preferred embodiment, the second layer includes fibroblasts.

The number of cells used in the homogenous cell mixture is higher than that seen in the prior art, and is thought to contribute to the in vitro cell sorting process. For example, $4 \times 10^6$ cells of each cell type are generally used. In a preferred embodiment, $4 \times 10^6$ fibroblasts are added to the homogenous cell mixture.

Additionally, the layered cell sorted tissue possesses an epidermal-dermal junction that is substantially similar in structure and function to its native counterpart. That is, the tissue expresses the necessary integral proteins such as hemidesmosomes and collagen I, collagen IV, and collagen VII, to attach the epidermal and dermal layers with the proper basement membrane morphology. As used herein, the term "basement membrane" also refers to the basal lamina and may be used interchangeably with the term "basal lamina." Therefore, the tendency of the layered cell sorted tissue to separate or "blister" is reduced in comparison to other tissue prototypes currently being marketed.

The layered cell sorted tissue may be formed to suit any particular arrangement of layers that is desired. In one embodiment, an epidermal layer is formed as the top layer of tissue. In another embodiment, the epidermal layer is the bottom layer of tissue.

The orientation of the cell layers is manipulated by contacting the homogenous mixture of cells with a connective tissue component during culturing. Connective tissue components that may be used are fibronectin, collagen IV, laminin, and mixtures thereof. Fibronectin is the preferred connective tissue component. The homogenous cell mixture sorts to form an epidermal layer that contacts the connective tissue component.

In one embodiment, the homogenous mixture of cells is added to a transwell membrane coated with fibronectin. The tissue that is formed is upside down, i.e., the epidermal layer is the bottom layer. In another embodiment, a solution of fibronectin is added to a homogenous mixture of cells. The tissue formed by this method has an epidermal layer that is on top.

In another embodiment, the layered cell sorted tissue may be used as a skin graft to treat traumatic wounds, burn injury, decubiti and other ulcerations due to such conditions as diabetes mellitus and chronic venous stasis. If used as a skin graft, the layered cell sorted tissue may be placed directly on the graft site. However, in another embodiment, a homogenous mixture of keratinocytes and fibroblasts may also be applied to the graft site and allowed to spontaneously sort into a discrete layer including keratinocytes and a discrete layer including fibroblasts.

In a further embodiment, the cell sorted tissue may be used in an in vitro assay to detect tissue responses to chemicals or drugs. Upon providing a cell sorted tissue, the tissue is contacted with the chemical or drug of interest. The response of the tissue to the chemical or drug is determined by comparing the effect of the chemical or drug on the phenotype, genotype, or both, between the tissue before and after contact with the chemical or drug.

In another embodiment, the layered cell sorted tissue is used as an in vitro assay for studying tumor cell metastasis, i.e., tumor cell invasion. Upon providing the layered cell sorted tissue on a light blocking plate such as a BD BioCoat FluorBlok plate (BD Biosciences, Bedford, Mass.), the tissue is contacted with the anti-metastatic compound to be tested. Fluorescently labeled tumor cells to be tested are also added to contact the tissue. After a suitable incubation period, the effect of the anti-metastatic compound on the tumor cells is then determined by measuring fluorescence at the bottom of the plate. Because of the light blocking qualities of the plate, only those tumor cells which have migrated through all tissue layers will be detected by the plate reader.

BRIEF DESCRIPTION OF THE DRAWINGS

The patent application contains at least one photograph executed in color. Copies of this patent with color photograph(s) will be provided by the Patent and Trademark Office upon request and payment of the necessary fee.

DETAILED DESCRIPTION OF THE INVENTION

Figure 1:
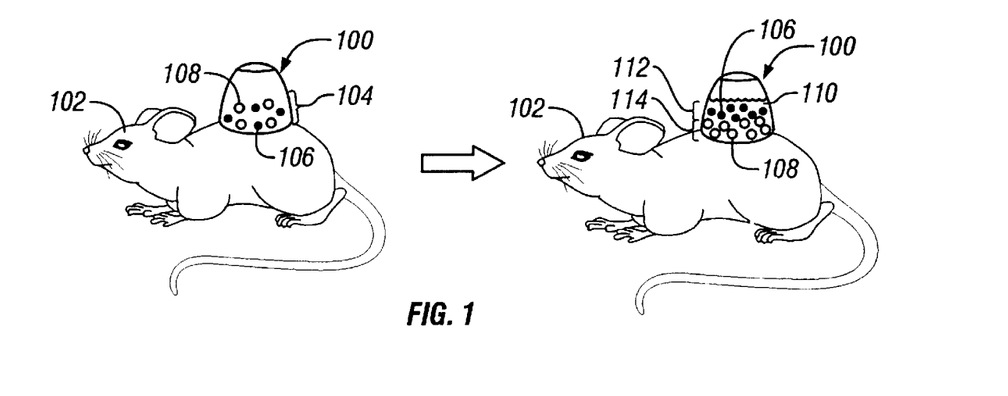
FIG. 1 demonstrates an in vivo method of creating a layered cell sorted tissue.

A layered cell sorted tissue and methods of creating the tissue in vivo were previously described in WO 99/45770. Briefly, as seen in FIG. 1, an inert silicon chamber 100 was implanted onto the back of a SCID (Severe Combined Immunodeficient) mouse 102, directly onto the muscle fascia, and a mixed cell slurry 104 including keratinocytes 106 and fibroblasts 108 was then placed into the chamber 100. As a result of the implant procedure, the chamber 100 filled with wound fluid 110, which primarily collected above the homogenous cell mixture 104 of keratinocytes 106 and fibroblasts 108. After one week, the top of chamber 100 was removed to allow drying of the cells. After a second week, a biopsy sample of the skin was obtained and examined. The sample demonstrated that the mixed cell slurry 104 had spontaneously sorted into a discrete epidermal layer 112 including keratinocytes 106 and a discrete dermal layer 114 including fibroblasts 108.

At a wound site, connective tissue is disrupted and fluid, i.e., wound fluid, begins to collect. Wound fluid includes many substances that promote the healing process. For example, there may be such substances as platelet-derived growth factor (PDGF), transforming growth factor-$\beta$ (TGF-$\beta$), and fibronectin in the fluid. The tissue repair mechanisms of the human body that promote wound healing also contribute to the process that organizes cells into functional structures. By identifying the specific factors that influence cell migration and organization, layered tissues may be formed in vitro that possess a structure that corresponds to their native counterpart. However, due to the abundance of growth factors and other proteins and cellular components involved in the in vivo wound healing process, it is not obvious which specific element(s) would best influence the sorting of cells in vitro.

In Vitro Layered Cell Sorted Tissue

The layered cell sorted tissues described herein include a discrete first cell layer and a discrete second cell layer that are formed in vitro by the spontaneous sorting of cells from a homogenous cell mixture. As used herein, the term "homogenous cell mixture" refers to a composition of single cells that includes different cell types. As used herein, the term "sort" or "sorted" refers to separation or arrangement of cells from a homogenous cell mixture. Furthermore, as used herein, the term "tissue" refers to an organized collection of cells specialized to perform a particular function. The cells may be of the same type or different types. The tissue may be structured to include two or more discrete cell layers arranged by cell type, e.g., skin. As used herein, the term "discrete" means distinct or clearly distinguishable. The layered tissue that is created also forms a basement membrane that has the necessary integral proteins, e.g., hemidesmosomes and intact collagen I and collagen IV filaments, and collagen VII, to create a junction substantially similar to native epidermal-dermal junctions in structure and function. In addition, keratin intermediate filaments made of keratins 5 and 14 reinforce the basal cell to basal cell keratinocyte interaction. Thus, layered cell sorted tissues of this invention are less likely to blister than prototypes currently on the market.

The cells that may be used to create layered cell sorted tissue in vitro include epithelial cells such as keratinocytes, but CaCo2 colon carcinoma cells, A431 vaginal carcinoma cells, and HUC18 urogenital cells may also be used. In general, epithelial cells as a class combined with mesenchymal cells as a class are suitable for making layered cell sorted tissues in vitro, with a variety of cell types representative of each class possible.

In a preferred embodiment, the layered cell sorted tissue has a second cell layer including fibroblasts, and a first cell layer made from keratinocytes. In another embodiment, fibroblasts remain as the second cell layer, but the first cell layer may include either CaCo2, A431, or HUC18 epithelial cells. In some instances it may be desirable to sort the cells so that a particular layer is on the top. As used herein, the term "top" means the surface lying opposite the transwell membrane or bottom of the culture dish. Either the first or second layer may be formed to be on top.

Cellular Components of In Vitro Layered Cell Sorted Tissue

The cells used to create layered cell sorted tissues in vitro are preferably derived from the same species. When used as a skin graft, it is preferred that the cells be derived from the same individual of the species to be treated. However, in some instances it is desirable to make a heterologous layered cell sorted tissue, i.e., with cells derived from different individuals or with cells derived from different species. For example, porcine tissue may be a potential universal donor for use in human applications.

In general, the cells used in making the layered cell sorted tissue in vitro are obtained from primary sources, i.e., an individual, or from a cell line maintained in tissue culture. In one embodiment, the cells are from the same individual or cell line. In another embodiment, the cells are from different individuals or cell lines and therefore have different genotypes. For use as a skin graft, the cells are generally autologous, but may also be allogenic, xenogenic, or any mixture thereof. The fibroblasts are preferably autologous. Furthermore, the cells may be treated or modified so as to be resistant to rejection by the host.

Methods for the isolation of cells are available to those skilled in the art. For example, skin cells can be isolated from intact skin tissue. Biopsies of skin can be used to isolate primary keratinocytes and fibroblasts. The source of skin may be from sources such as young skin, old skin, foreskin, skin from mammoplasties or abdominoplasties, and skin from facelifts. The skin samples can also be taken from patients with skin diseases, and the resulting skin made in vitro will reflect the disease phenotype of the skin biopsy.

In general, if using keratinocytes, they should be obtained preferably from passage 3, more preferably from passage 2 due to the desirability of maintaining the basal keratinocyte population. Furthermore, the number of cells cultured to form the layered cell sorted tissue is high, preferably at least $4 \times 10^6$ cells of each cell type. At this cell concentration, it is thought that the factors responsible for cell sorting are maintained at a very high concentration. In contrast, organotypic cultures, for example, use only 0.35 to $0.75 \times 10^6$ fibroblasts and 0.25 to $0.5 \times 10^6$ keratinocytes, which are seeded on top of the fibroblast layer.

Methods for Forming Layered Cell Sorted Tissue In Vitro

Fibronectin, a known component of connective tissue, was studied in this invention for its effects on in vitro cell sorting. The role of fibronectin in facilitating cell sorting was previously unknown. The fibronectin was either coated on a transwell membrane or added to the medium above the cell slurry. Other connective tissue components may be used in the method of this invention. For example, collagen IV and laminin, or more complex mixtures, such as matrigel, may also be used as connective tissue components.

In one embodiment, the in vitro method for generating a layered cell sorted tissue includes contacting a cell slurry with a connective tissue component, then allowing the mixture to spontaneously sort into discrete first and second layers or more, depending on the number of cell types. As used herein, the term "cell slurry" refers to a composition comprising a homogenous mixture of cells. The cell layer containing epidermal cells was found to form so that it contacted the connective tissue component.

Figure 2:
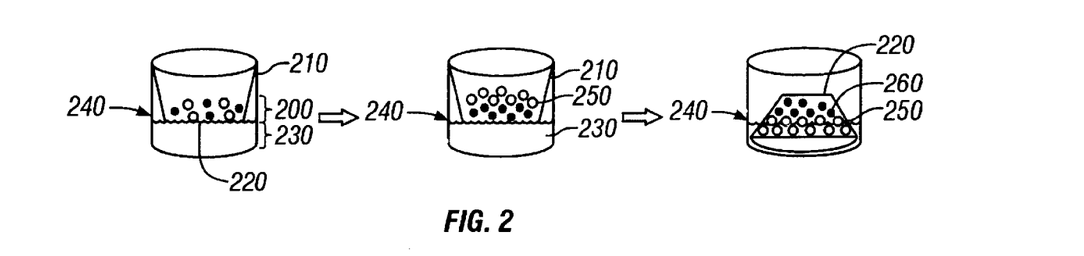
FIG. 2 shows an in vitro method of creating a layered cell sorted tissue using a transwell membrane coated with fibronectin.

In FIG. 2, the layered cell sorted tissue was made in vitro from a cell slurry of keratinocytes and fibroblasts 200 that was added onto a transwell insert 210. The transwell contains a porous membrane 220 that provides support for the skin cells while allowing them to be fed from culture medium 230 in contact with the membrane contained in the well beneath 240. If the membrane 220 is coated with a connective tissue component such as fibronectin, than the layered cell sorted tissue that forms is upside down in the sense that the epidermal keratinocytes attach to the membrane 220, and the dermal fibroblasts form a discrete layer 250 above them. The transwell insert can be inverted after the initial formation of tissue to set the tissue right side up, i.e., the membrane 220 is at the top and epidermis 260 is attached to it with dermis 250 attached under that. Culture medium 230 can then bathe the tissue from underneath, while the membrane 220 can be exposed to the air to provide the crucial air-liquid interface to induce differentiation of the epidermis.

Figure 3:
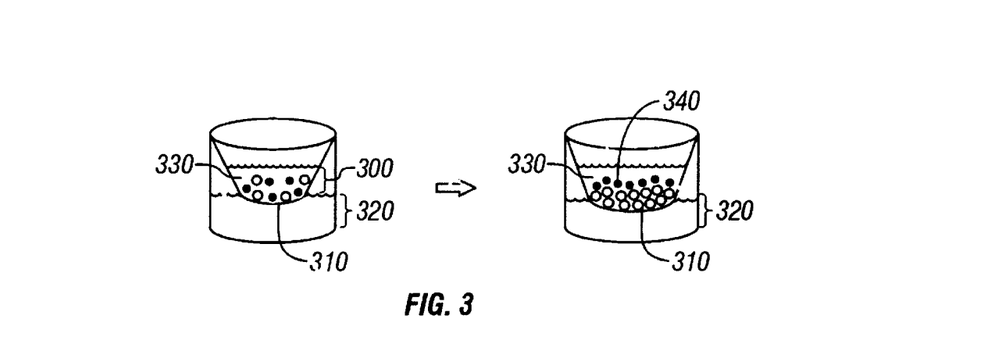
FIG. 3 shows an in vitro method of creating a layered cell sorted tissue by placing fibronectin on top of the cell slurry.

In FIG. 3, another embodiment of the in vitro method is demonstrated by setting up a similar system as shown in FIG. 2, but without the fibronectin coating on the membrane. In this case, the cell slurry 300 is added onto a transwell insert membrane 310 without the fibronectin coating. Culture medium 320 feeds the cells from underneath, while another fluid containing fibronectin (analogous to wound fluid) 330 sits above the cell slurry. In this case the layered cell sorted tissue forms right side up, with keratinocytes 340 in contact with the fibronectin containing fluid 330 present above them.

Figure 4A:
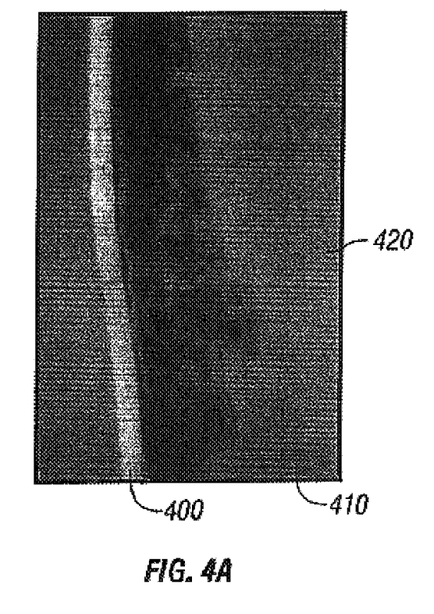
FIGS. 4A and 4B are photographs of an H/E stained, paraffin-embedded cross-section of a layered cell sorted tissue made by the method exemplified in FIG. 2.
Figure 4B:
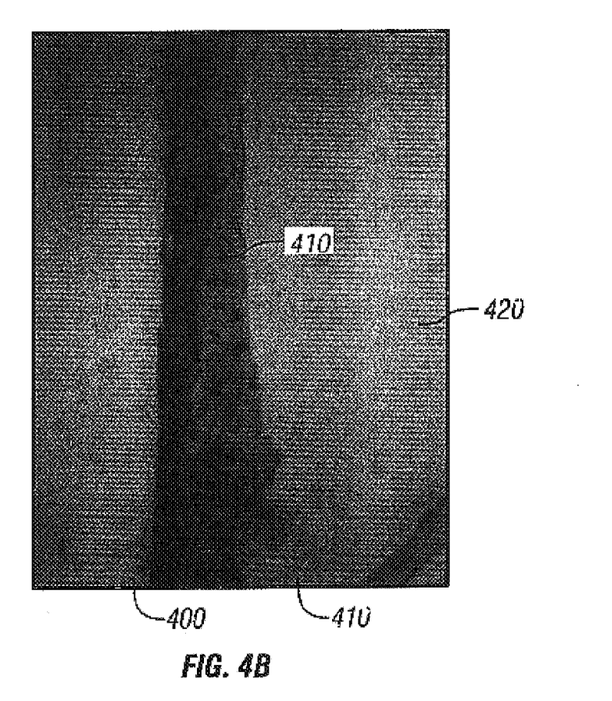

FIGS. 4A and 4B are digital photographs of a Leitz microscopic image of an H/E stained, paraffin-embedded cross-section of the transwell membrane and subsequently formed cell sorted tissue by the method depicted in FIG. 2. Visible at the top is a cross-section of the membrane support 400. Attached are a layer of violet stained cells 410 that are keratinocytes of the restructured epidermis. Below these are pink stained cells 420 that are the dermal fibroblasts. Importantly, the cells are separated into discrete layers of epidermal and dermal cells by a process of spontaneous cell sorting and formation of a basement membrane.

Applications of Layered Cell Sorted Tissues

The layered cell sorted tissues described herein may be used as an artificial tissue for any mammal. Humans are the preferred mammal. However, the invention may be practiced with other mammals such as non-human primates and members of the bovine, ovine, porcine, equine, canine, and feline species as well as rodents such as mice, rats, and guinea pigs, and members of the lagomorph family including rabbits. The particular layered cell sorted tissue which is formed is generally dependent on the source of cells, but may not be. For example, when human cells are used, a human layered cell sorted tissue is formed.

One benefit of cultivating the layered cell sorted tissues in vitro is that they are made under sterile conditions, and they are not contaminated by cells or factors contributed by a host animal to grow up a graft. Thus, in one embodiment, the layered cell sorted tissue made in tissue culture may be used as a skin graft that could be used on graft sites such as traumatic wounds and burn injury. The skin grafts may also be used to cover decubiti and ulcerations secondary to diabetes mellitus and venous stasis. If cultivated with the dermal layer on top, the graft may be flipped to orient the epidermal layer as the top layer of the graft during graft placement. In another embodiment, a homogenous mixture of keratinocytes and fibroblasts is added to a graft site. The cell slurry then spontaneously sorts into discrete keratinocyte and fibroblast layers. The fibroblasts also slowly lay down extracellular matrix material and therefore, the dermis becomes more acellular.

In a further embodiment, the layered cell sorted tissues of this invention may be used in assays to test tissue responses to chemicals or drugs such as, but not limited to, those used in the cosmetic or petroleum industries. Upon providing a layered cell sorted tissue, formed as described above, the tissue is contacted with the chemical or drug of interest. The difference in phenotype, genotype, or both between the tissue before and after exposure to the chemical or drug is then compared to determine the response of the tissue to that chemical or drug.

In another embodiment, the layered cell sorted tissues may serve as an in vitro model or assay for tumor cell metastasis. Current in vitro models for tumor metastasis employ cell monolayers. The tissue of this invention mimics the structure of native tissue, i.e., multiple layers, and thus provides a superior assay by which to study the metastatic process as it occurs in the human body. Cells such as microvascular endothelial cells or smooth muscle cells may be used to form one of the layers in the layered cell sorted tissue. In such a method, the layered cell sorted tissue would be placed in a multiwell that blocks the transmission of fluorescent light, such as a BD BioCoat FluoroBlok plate (BD Biosciences, Bedford, Mass.). The tissue would then be contacted with an anti-metastatic compound and at least one fluorescently labeled or marked tumor cell. After the appropriate incubation period, the assay would determine whether the anti-metastatic activity of the compound in question had an anti-metastatic effect by measuring fluorescence at the bottom of the plate before and after contact of the tissue with the anti-metastatic compound. Because of the light blocking qualities of the plate, only those labeled cells which have migrated through all tissue layers will be detected by the plate reader.

EXAMPLES

Example 1

Preparation of Skin Cells

Briefly, newborn foreskin was trimmed, cut into small pieces, and placed in dispase at 4° C. overnight. The dispase-treated foreskin was transferred into new petri dishes and washed with phosphate buffered saline. Epidermis was physically separated from dermis with forceps and treated with 0.3% trypsin at 37° C. for 30 minutes. The trypsin was then neutralized with soybean trypsin inhibitor (Sigma, St. Louis, Mo.). The detached keratinocytes were collected using a clinical centrifuge. The keratinocyte pellet was resuspended in SFM (Gibco-BRL, Grand Island, N.Y.) media, and plated on collagen coated dishes. After 3–4 days, medium to large colonies of primary keratinocytes were visible (10–20 cells large), and the plates were refed with SFM. After 7 days the plates were then split 1:3 using standard trypsinization methods. The keratinocytes were then cultured for two to three passages in a 37° C. incubator with 5% $CO_2$ then used in the formation of a layered cell sorted skin.

Primary fibroblast cultures were obtained from the remaining dermis by plating the separated dermis in six well plates in the presence of DMEM (Gibco-BRL) with 10% calf serum for approximately 1 week. The cells that grew away from the dermal explants were fibroblasts. Fibroblasts were passaged in DMEM with 10% fetal bovine serum for use in the formation of a layered cell sorted artificial skin.

Example 2

Medium Used to Feed Skin Cells

The medium used to grow the in vitro layered cell sorted skin is also an important variable. The components of the medium compatible with the formation of dermal and epidermal layers is listed below.

500 ml DMEM (Gibco-BRL cat. no. 11965-092, Grand Island, N.Y.

10 ml penicillin/streptomycin

Add fetal bovine serum to 10% volume

Example 3

Method for Making Layered Cell Sorted Skin In Vitro

Transwells were first prepared by coating them with 5 µg/ml fibronectin from human plasma (Sigma, St. Louis, Mo.) and incubating them at 37° C. for 30 minutes. In one centrifuge tube, $4\times10^6$ keratinocytes and $4\times10^6$ fibroblasts were combined, gently mixed, and then centrifuged. Media was then removed without disturbing the cell pellet and the cell pellet incubated on ice for 30 minutes. The cell pellet was then resuspended in an approximately equal volume (50–100 µl) of DMEM with 10% fetal bovine serum (FBS) to create a cell slurry. The resuspended cell slurry was seeded onto the transwell and fed using DMEM with 10% FBS. If the epidermal layer was desired on the membrane, then the culture well and transwell were both fed. However, if epidermis was desired on top, then only the transwell was fed for 24 hours. After that, both wells could be fed. The cells were fed as needed for the first 1 to 3 days, then every other day from that point on. In general, the incubation conditions were at 37° C. and 5% $CO_2$ for 7 to 14 days depending on the assay for which the tissue would be used.

Figure 5A:
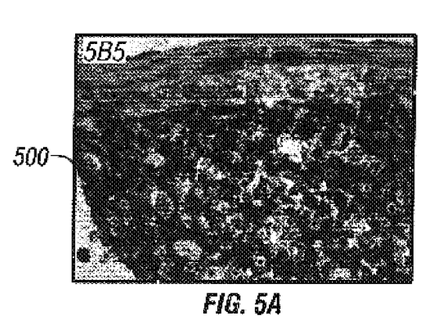
FIGS. 5A-5F are photographs of an immunohistochemically stained layered cell sorted tissue that show discrete epidermal and dermal layers, and a continuous basement membrane (epidermal-dermal junction).
Figure 5B:
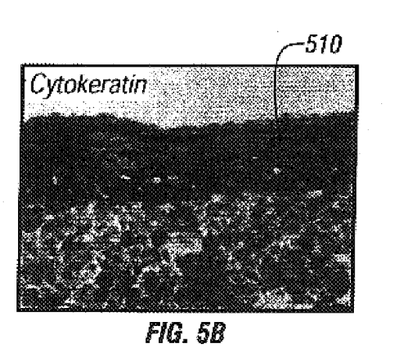
Figure 5C:
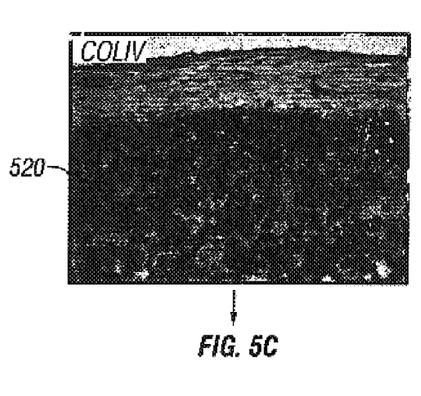
Figure 5D:
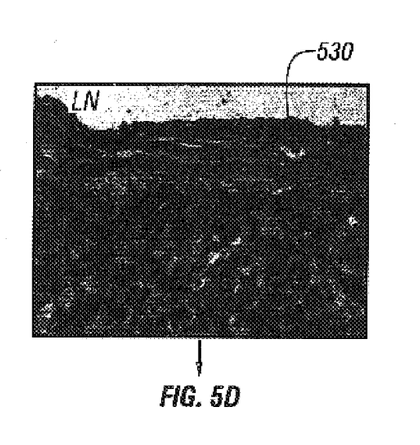
Figure 5E:
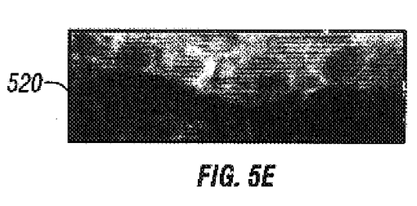
Figure 5F:
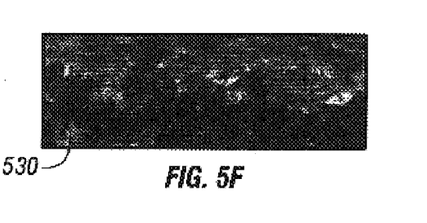
Figure 6A:
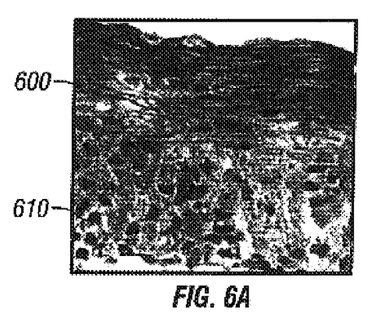
FIGS. 6A-6D are photographs of H/E stained 6 μm sections of various layered cell sorted tissues.

As seen in FIGS. 5A-5F, immunohistochemical staining of a layered cell sorted skin made in vitro identified discrete epidermal and dermal layers, and an epidermal-dermal junction. In FIG. 5A, staining of the cell sorted tissue with a 5B5 human fibroblast specific antibody clearly delineates the dermal layer 500. In FIG. 5B, an antibody against a panel of cytokeratins clearly shows the epidermal layer 510. Junctional (basement membrane) staining with a collagen IV antibody in FIG. 5C demonstrates a discrete epidermal-dermal junction 520 which is magnified in FIG. 5E. Staining with a human laminin antibody also shows a discrete epidermal-dermal junction 530 in FIG. 5D which is magnified in FIG. 5F. FIG. 6A further shows the discrete epidermal 600 and dermal 610 layers of the layered cell sorted skin.

Example 4

Fixation and Imaging of Layered Cell Sorted Skin

Evaluation of layer formation requires fixation and cross-sectioning of samples. The transwell inserts containing the cell sorted skin were placed on a glass slide. After removal of excess medium above the cells, a buffered 10% formalin solution was dropped directly onto the cell samples in the transwells and incubated for 10 minutes. The membranes were then cut away from the transwell inserts with a scalpel and placed in glass vials containing 1 ml of buffered 10% formalin. The samples were then paraffin embedded, thin sectioned, and stained with hemotoxylin/eosin for examination under a compound microscope to discern the extent of formation of two distinct cell layers. The microscopic images were captured by digital photography with a Nikon Coolpix 990, as shown in FIGS. 4A and 4B.

Example 5

Layered CaCo2 Cell Sorted Tissue

CaCo2 colon carcinoma cells were cultured using the technique described in Trainer et al., *Int. J. Cancer* 287–296

(1988) and harvested using a standard trypsinization method. Similarly, fetal fibroblasts were harvested as described in example 1.

Transwells were first prepared by coating the transwell membrane with growth factor reduced Matrigel (BD Biosciences, Bedford, Mass.) and incubating them at 37° C. for 30 minutes. At the end of the incubation period, all visible Matrigel was removed from the membrane, leaving only a thin coating of laminin and collagen IV (alternatively coating with individual solution of collagen IV and laminin may also be done). In one centrifuge tube, $4 \times 10^6$ CaCo2 cells and $4 \times 10^6$ fibroblasts were combined, gently mixed, and then centrifuged. Media was then removed without disturbing the cell pellet and the cell pellet incubated on ice for 30 minutes. The cell pellet was then resuspended in an approximately equal volume (50–100 $\mu$l) of DMEM with 10% FBS to create a cell slurry. The resuspended cell slurry was then seeded onto the transwell membrane and fed using DMEM with 10% FBS. Both the transwell and culture well were fed. The cells were fed as needed for the first three days and from that point on, every other day. Incubation conditions were the same as in example 3.

Figure 6B:
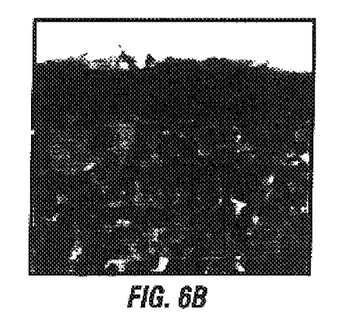
Figure 6C:
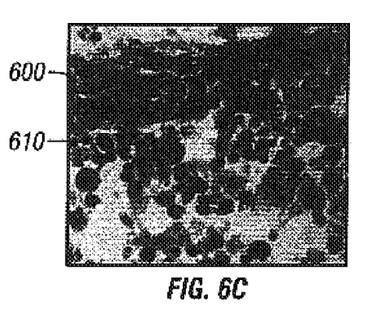

FIG. 6C demonstrates the discrete epidermal 600 and dermal 610 layers in the layered CaCo2 cell sorted tissue.

Example 6

Layered A431 Cell Sorted Tissue

A431 vaginal carcinoma cells were cultured using the technique described in Faust et al., *Cancer Res.* 52:2460–2463 (1992) and harvested using a standard trypsinization method. Similarly, fetal fibroblasts were harvested as described in example 1.

Transwells were first prepared by coating the transwell membrane with growth factor reduced Matrigel (BD Biosciences, Bedford, Mass.) and incubating them at 37° C. for 30 minutes. At the end of the incubation period, all visible Matrigel was removed from the membrane, leaving only a thin coating of laminin and collagen IV. In one centrifuge tube, $4 \times 10^6$ A431 cells and $4 \times 10^6$ fibroblasts were combined, gently mixed, and then centrifuged. Media was then removed without disturbing the cell pellet and the cell pellet incubated on ice for 30 minutes. The cell pellet was then resuspended in an approximately equal volume (50–100 $\mu$l) of DMEM with 10% FBS to create a cell slurry. The resuspended cell slurry was then seeded onto the transwell membrane and fed using DMEM with 10% FBS. Both the transwell and culture well were fed. The cells were fed as needed for the first three days and from that point on, every other day. Incubation conditions were the same as in example 3.

Figure 6D:
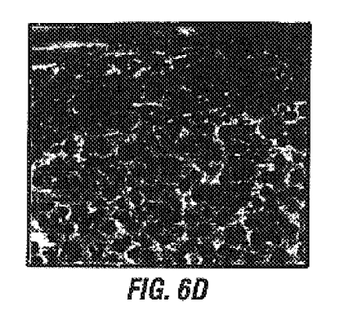

FIG. 6D shows the discrete epidermal 600 and dermal 610 layers of the layered A431 cell sorted tissue.

Example 7

Layered HUC18 Cell Sorted Tissue

HUC18 urogenital cells were cultured using the technique described in Meyers C., *Methods In Cell Science* 18:201–210 (1996), and harvested using a standard trypsinization method. The keratinocytes and fibroblasts were harvested as described in example 1.

Transwells were first prepared by coating them with 5 $\mu$g/ml fibronectin (Sigma, St. Louis, Mo.) and incubating them at 37° C. for 30 minutes. In one centrifuge tube, $1.2 \times 10^6$ keratinocytes (30%), $2.8 \times 10^6$ HUC18 cells (70%), and $4 \times 10^6$ fibroblasts were combined, gently mixed, and then centrifuged. Media was then removed without disturbing the cell pellet and the cell pellet incubated on ice for 30 minutes. The cell pellet was then resuspended in an approximately equal volume (50–100 $\mu$l) of DMEM with 10% FBS to create a cell slurry. The resuspended cell slurry was seeded onto the transwell and fed using DMEM with 10% FBS. Both the transwell and culture well were fed. The cells were fed as needed for the first three days and from that point on, every other day. Incubation conditions were the same as in example 3.

FIG. 6B shows the discrete epidermal 600 and dermal 610 layers of the layered HUC18 cell sorted tissue.

Example 8

In Vitro Model for Tumor Metastasis

Keratinocytes and fibroblasts were harvested using the technique described in example 1.

Fibrillar collagen coated multiwell plates (BioCoat FluorBlok plates, BD Biosciences, Bedford, Mass.) were first prepared by coating with 5 $\mu$g/ml fibronectin and incubating them at 37° C. for 30 minutes. In one centrifuge tube, $4 \times 10^6$ keratinocytes and $4 \times 10^6$ fibroblasts were combined, gently mixed, and then centrifuged. Media was then removed without disturbing the cell pellet and the cell pellet incubated on ice for 30 minutes. The cell pellet was then resuspended in an approximately equal volume (50–100 $\mu$l) of DMEM with 10% FBS to create a cell slurry. The resuspended pellet was then seeded onto the FluoroBlok wells and fed using DMEM with 10% FBS in both the culture wells and the insert wells. The cells were fed as needed for the first 3 days and from that point on, every other day. As in example 3, the incubation conditions were at 37° C. and 5% $CO_2$ for 7 to 14 days. After that, the serum concentration in the wells was gradually reduced by 50% per day for days 7–10. The cells were then cultured in serum free media from the tenth day.

Media was then removed and the compound to be tested for anti-metastatic effects was added along with DMEM with 5% FBS. $2.5 \times 10^4$ HT-1080 cells (human fibrosarcoma) labeled with fluorescent dye were then placed into the insert wells with the cell sorted tissue. Other appropriate metastatic cells may be used. The cells were then incubated for 20–22 hours at 37° C. Thereafter, the media was removed from the insert wells, and the plate transferred to a second 24-well plate containing 0.5 ml/well of 4 $\mu$g/ml Calcein AM in Hanks buffered saline and incubated for 1 hour at 37° C. The plate was then analyzed using a fluorescent plate reader at 485 nm excitation and 530 nm emission.

What is claimed is:

1. An in vitro method of generating a layered cell sorted tissue comprising a discrete first cell layer and a discrete second cell layer comprising the steps of:
   providing a homogenous mixture of cells, said mixture comprising epithelial cells and mesenchymal cells; and
   contacting said mixture with a membrane or a connective tissue component under conditions where said mixture spontaneously sorts into said first and second discrete cell layers,
   wherein said discrete first layer comprises epithelial cells and said second discrete cell layer comprises mesenchymal cells.

2. The in vitro method of claim 1 wherein said connective tissue component is fibronectin.

3. The in vitro method of claim 1 wherein said connective tissue component is a mixture of collagen IV and laminin.

4. The in vitro method of claim 1 wherein the step of contacting comprises placing said connective tissue component on top of said mixture.

5. The in vitro method of claim 1 wherein the step of contacting comprises adding said mixture to a membrane coated with said connective tissue component.

6. The method of claim 1 wherein said epithelial cells are keratinocytes.

7. The method of claim 1 wherein said epithelial cells are colon epithelial cells.

8. The method of claim 7 wherein said colon epithelial cells are CaCo2 cells.

9. The method of claim 1 wherein said epithelial cells are vaginal epithelial cells.

10. The method of claim 9 wherein said vaginal epithelial cells are A431 cells.

11. The method of claim 1 wherein said epithelial cells are urogenital epithelial cells.

12. The method of claim 11 wherein said urogenital epithelial cells are HUC18 cells.

13. The method of claim 1 wherein said mesenchymal cells are fibroblasts.

14. The method of claim 1 wherein said first cell layer is an epidermal layer comprising keratinocytes and said second cell layer is a dermal layer comprising fibroblasts.

15. The method of claim 14 further comprising a plurality of integral proteins that connect said epidermal and dermal layers to form a basal lamina.

16. The method of claim 14 wherein the epidermal layer is the top layer of said tissue.

17. The method of claim 14 wherein the epidermal layer is the bottom layer of said tissue.

18. The method of claim 14 wherein said layered cell sorted tissue is a skin graft.

19. The method of claim 1 wherein said connective tissue component is a mixture of collagen IV.

20. The method of claim 1 wherein said connective tissue component is a mixture of laminin.

* * * * *